United States Patent
Lin (10) Patent No.: US 8,523,825 B2
(45) Date of Patent: Sep. 3, 2013

(54) DISPENSER DEVICE

(75) Inventor: Tsai-Ming Lin, Kaohsiung (TW)

(73) Assignee: Dermato-Plastica-Beauty (DPB), Kaohsiung (TW)

( * ) Notice: Subject to any disclaimer, the term of this patent is extended or adjusted under 35 U.S.C. 154(b) by 19 days.

(21) Appl. No.: 12/929,175

(22) Filed: Jan. 6, 2011

(65) Prior Publication Data

US 2011/0282299 A1 Nov. 17, 2011

(30) Foreign Application Priority Data

May 17, 2010 (TW) .............................. 99209214 U (51) Int. Cl.
*A61M 5/00* (2006.01)
*A61M 31/00* (2006.01)
*A61M 5/315* (2006.01)
*A61M 5/31* (2006.01)

(52) U.S. Cl.
USPC .............. 604/188; 604/61; 604/63; 604/181; 604/187; 604/218; 604/223; 604/227; 604/228; 604/232; 604/234; 604/235; 604/240; 604/242; 604/243

(58) Field of Classification Search
USPC ................... 604/57, 59, 60, 61, 63, 134, 135, 604/151, 152, 153, 154, 155, 181, 187, 188, 604/207, 208, 209, 210, 211, 218, 223, 227, 604/228, 232, 234, 235, 240, 241, 242, 243
See application file for complete search history.

(56) References Cited

U.S. PATENT DOCUMENTS

| | | | | |
|---|---|---|---|---|
| 5,062,837 A | * | 11/1991 | Al-Sioufi et al. | ............. 604/240 |
| 6,213,971 B1 | * | 4/2001 | Poole | .............................. 604/35 |
| 7,632,251 B2 | * | 12/2009 | Lin et al. | ........................ 604/187 |

* cited by examiner

*Primary Examiner* — Kevin C Sirmons
*Assistant Examiner* — Shefali Patel
(74) *Attorney, Agent, or Firm* — Leong C. Lei (57) ABSTRACT

A dispenser device comprising a pistol housing, a needle direction control mechanism, a boost mechanism, a quantification control mechanism, and a combination of the pistol housing, the needle direction control mechanism, the boost mechanism, and a syringe positioning mechanism or a holding ring embodies the present invention with features and advantages shown as follows, (1) Uniform injection of agents synchronously mixed by not less than two contents; (2) Mixed agents not exposed in air; (3) Uniform injection, high air tightness, injection direction controlled by easy turning, smooth and convenient operation, high powerful operation via shifts of a push rod driven by a pressed trigger, promoted yield rate, assembly easily constructed, reduced manufacture cost, and convenient maintenance.

9 Claims, 6 Drawing Sheets

DISPENSER DEVICE

CROSS REFERENCE TO RELATED APPLICATIONS

This application claims foreign priority to Application number 099209214, filed in Taiwan on May 17, 2010.

BACKGROUND OF THE INVENTION (1) Field of the Invention

The present invention relates to a dispenser device, especially to an easily-controlled dispenser device with adjustable injecting direction, accurate, precise and uniform volume per-injection.

(2) Prior Art Description

Since the first report on fat grating appeared in medical literature by Dr. Neüber in 1893, autologous fat graft serving as a soft tissue filler was performed by many surgeons to fill (or level) depressed scars, minimize facial wrinkles, rejuvenate facial contours, and even reinforce external shape of lips or nasion for over one century[1]. The fat grafting was regarded for years as an excellent procedure for reconstructing soft tissue defects or as an autologous filler, and thus has been applied in fields of reconstructive, aesthetic and plastic surgery.

A successful fat grafting surgery depends on four major steps during the procedure: harvesting of fat, processing of fat, refinement of fat and transplantation of the purified fat, which is the final and cardinal step of all[2,3]. Surgeons and scientists in this field have proposed various fat grating techniques; however, no convincing resolutions have been concluded yet[4-19]. The transplantation of fat requires the delicate hand-operation of an experienced surgeon. Therefore, the key to the high fat survival rate with low morbidity is critically dependent on surgeon's skill to inject minute volume of the fat if needed. An appropriate instrument is thus desirable for a surgeon to perform a successful procedure as such. On the other hand, morbidities of fat grafting such as absorption, infection, embolism, cyst formation, calcification, ossification, necrosis, asymmetry, skin necrosis/fistula formation, iatrogenic neurovascular injuries are closely correlated with improper, uneven, or most oftentimes, excessive transplantation of fat during the fat grafting procedure[20].

Dr. Coleman, the renowned American plastic surgeon, proposed the concept of "Structure Fat Graft" which emphasized that the fat parcel should be layer by layer arranged with the injection volume less than 1/10 cc per parcel (even 1/30~1/50 cc is requested in special site such as peri-orbital areas)[21]. By avoiding the central necrosis of fat graft induced by over-injection in each parcel, the complications and morbidities of fat grafting will be minimized.

Dr. Carpaneda in Brazil pointed out about 40% survival tissue was observed within the peripheral zone (1.5±0.5 mm to peripheral margin) in his eminent article[4]. He addressed later that thickness and geometrical shape are the key factors to a successful fat transplantation and concluded that the radius of fat graft either in spherical shape or cylindroid shape should be less than 2 mm to get a higher fat survival rate[22]. Based on the theory postulated by Carpaneda, the volume of fat could be calculated (if each fat droplet is presumed to be a spherical shape) with the following formula:

The volume of a Globe with 1.0 mm in radius is 4.2 mm³
The volume of a Globe with 1.5 mm in radius is 14.1 mm³
The volume of a Globe with 2.0 mm in radius is 33.5 mm³
The Volume of a globe is calculated by $(4/3)\pi r^3$, r: Global radius

| Global radius | Global volume | Injection frequency per 1 cc (1000 mm³) fat graft |
|---|---|---|
| 1.0 mm | 4.2 mm³ | 240 |
| 1.5 mm | 14.1 mm³ | 70 |
| 2.0 mm | 33.5 mm³ | 30 |

Consequently, in fat grafting the minimal injection frequency should be at least 30 per cc to achieve the best survival rate.

Although there are devices in the market to assist the surgeon, the optimal device currently available has a per-injection volume of up to 1/10 cc (some may even yield as high as 0.5 or 1 cc per-injection!)[23-24]. An assumed successful surgery may end up in vain due to the lack of ideal tools. This situation reflects what Faith Baldwin has said "Character builds slowly, but it can be torn down within incredible swiftness."

The DISPOS-A-JECT™ SYSTEM series from Byron Medical, delivers 0.1 cc with each pull of trigger[23], which will cause inevitable morbidities/complication of fat grafting surgery and thus is not well accepted by surgeons. Cytori Therapeutic., producer of the innovative PureGraft™ system for fat grafting, claims its CellBrush™ a cutting edge device for the surgeons to yield a promising result in fat grafting at a 0.15 cc per injection[25]. However, the critical requirement for a successful fat grafting is not met yet. That is, to deliver every fat droplet at a volume between 1/30 cc and 1/240 cc as evidenced in literature and practical medicine[4,22].

Byron Medical supplies DISPOS-A-JECT™ SYSTEM (FIG. 1) with a minimum volume of 1/10 cc per-injection, which fails to meet the basic requirement of a smaller volume, i.e. 1/30 cc to 1/50 cc, per-injection, Besides, this system uses exclusively 1 cc BD Luer-Lok syringes. The lack of the flexibility in the choice of regular Luer-Slip 1 cc syringes available in any hospital or clinic could cause inconvenience and unpopularity.

Figure 1:
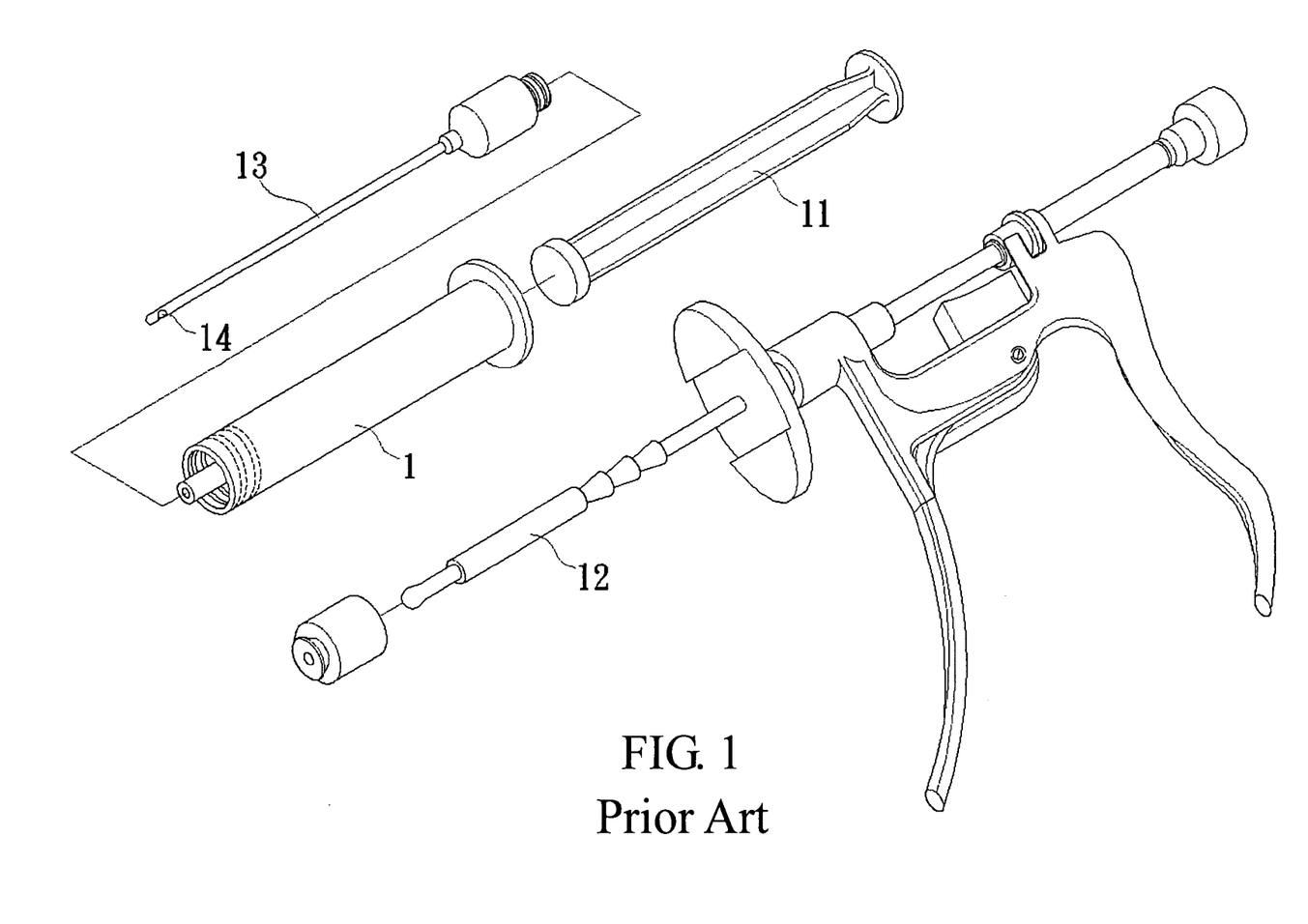
FIG. 1 is exploded views of components of a dispenser device manufactured in prior arts.

Referring to FIG. 1 for DISPOS-A-JECT™ SYSTEM operated in fat graft surgery: the SYSTEM adapter (12) in place of a plunger (11) removed from a syringe (1) in advance is jointed to the syringe (1) for propelling fat inevitably exposed in air which raises doubts about fat cells infected and a lower survival rate. Furthermore, a fixed angle between the SYSTEM gun's surface and an infiltration cannula (13) (or a pinhole (14)) is detrimental to surgery's flexible adjustment in injection angles and hence causes a deviated injection plane or failure of injection during surgery for fat injected clinically.

Recent articles have proved that concurrent injection of human adipose-derived stem/stromal cells (ADSCs) with fat graft promotes efficiently the fat survival rate[19,26]. Adding nutritious medium or platelet-rich plasma (PRP) which is rich in variable growth factors and cytokines is reported to enhance the survival of the fat[27]. However, the even mixture of fat graft with ADSCs, medium or PRP is not easily attainable. A debating issue in practice such as unevenly-distribution of the additives could give rise to a failure for optimal effect.

With the above disclosure, a new device developed for fat graft to overcome various drawbacks from prior arts is indispensable to fulfill the requirements for precise volume control, airtight equipment, convenient operation, cost effectiveness, and micro-dosage (between 1/30 and 1/240 cc per-injection) along with other considerations such as combined evenly transplantation of cells (e.g., stem cells), biomaterials, or growth factors. Note:

[1] Neüber, F. Fettgraftation. Zentrabl. Chir. 22: 66, 1893.
[2] Sommer, B. and Sattler, G. Current concepts of fat graft survival: histology of aspirated adipose tissue and review of the literature. Dermatol. Surg. 26: 1159, 2000.
[3] Katz, A. J. A novel device for the simple and efficient refinement of liposuctioned tissue. Plast. Reconstr. Surg. 107: 595, 2001.
[4] Carpaneda, C. A. Study of the histologic alterations and viability of the adipose graft in humans. Aesthet. Plast. Surg. 17: 43, 1993.
[5] Sattler, G. and Sommer, B. Liporecycling: a technique for facial rejuvenation and body contouring. Dermatol. Surg. 26: 1140, 2000.
[6] Sommer, B. and Sattler, G. Current concepts of fat graft survival: histology of aspirated adipose tissue and review of the literature. Dermatol. Surg. 26: 1159, 2000.
[7] Yaron, H. S. An integrated approach for increasing the survival of autologous fat grafts in the treatment of contour defect. Plast. Reconstr. Surg. 104: 945, 1999.
[8] Gonzalez, A. M. An alternative method for harvest and processing fat grafts: an in vitro study of cell viability and survival. Plast. Reconstr. Surg. 120: 285, 2007.
[9] MacRae, J. W. Ex vivo fat graft preservation—effects and implications of cryopreservation. Ann Plast Surg. 52: 281, 2004.
[10] Katz, A. J. A novel device for the simple and efficient refinement of liposuctioned tissue. Plast. Reconstr. Surg. 107: 595, 2001.
[11] Donofrio, L. M. Structural autologous lipoaugmentation: a pan-facial technique. Dermatol. Surg. 26: 1129, 2000.
[12] Coleman, S. R. Structural Fat Grafting. St. Louis, Mo.: Quality Medical, 2004. Pp. 30-175.
[13] Guerrerosantos, J. Aesthetic facial contour augmentation with microlipofilling. Aesthet. Surg J. 23: 239, 2003.
[14] Pu, Lee. L. Q. Long-term preservation of adipose aspirates after conventional lipoplasty. Aesthet. Surg J. 24: 536, 2004.
[15] Shiffman, M. A. and Mirrafati, S. Fat transfer techniques: the effect of harvest and transfer methods on adipocyte viability and review of the literature. Dermatol. Surg. 27: 819, 2001.
[16] Rohrich. R. J. The fat compartments of the face anatomy and clinical implications for cosmetic surgery. Plast. Reconstr. Surg. 119: 2219, 2007.
[17] Chajchir, A. and Benzaquen, I. Fat-grafting injection for soft-tissue augmentation. Plast. Reconstr. Surg. 84: 921, 1989.
[18] Testsuo, S. and Samuel M. L. Liposuction and lipotransplants for facial rejuvenation in the Asian patient. International J. Cosmet. Surg. Aesthet. Dematol. 5: 165, 2003.
[19] Yoshimura, K. Cell-assisted lipotransfer for cosmetic breast augmentation: supportive use of adipose-derived stem/stromal cells. Aesthet. Plast. Surg. 32: 48, 2008.
[20] Khawaja H. A. Fat Transfer Review: Controversies, Complications, Their Prevention, and Treatment. Int. J. Cosmet. Surg. 4: 131, 2002.
[21] Coleman, S. R. The technique of periorbital lipoinfiltration. Oper. Tech. Plast. Reconstr. Surg. 1: 120, 1994.
[22] Carpaneda, C. A., and Riberio, M. T. Percentage of graft viability versus injected volume in adipose autografts. Aesthet. Plast. Surg. 18: 17, 1994.
[23] http://www.byrondirect.com/download/downloads/Catalog/Subsecti ons/Micro-Infiltration.pdf
[24] Fulton, J. E. Breast Contouring with "Gelled" Autologous Fat: A 10-Year Update. Int. J. Cosmet. Surg. Aesth. Dermatol. 5: 155, 2003
[25] http://www.cytori.com/Store/ProductDetail.aspx?-ProductId=5&Pro ductFamilyId=4&Reload=1
[26] Yoshimura, K. Progenitor-Enriched Adipose Tissue Graftation as Rescue for Breast Implant Complications. Breast J. 12: 169, 2009.
[27] Cerervelli, V. Autologous platelet-rich plasma mixed with purified fat graft in aesthetic plastic surgery. Aesthet. Plast. Surg. 33: 716, 2009.

SUMMARY OF THE INVENTION

The principal object of the present invention to solve issues mentioned hereinabove is to supply one dispenser device comprising a pistol housing, a needle direction control mechanism, a boost mechanism, a quantification control mechanism, and a syringe positioning mechanism wherein the syringe positioning mechanism fixed on the pistol housing and coupled with the rear end of the needle direction mechanism has two syringe inlets at least in which there is a syringe inlet jointed to one of them. As a result, being characteristic of even injection and high air-tightness, the dispenser device is capable to synchronously and evenly inject one agent with not less than two contents mixed but without the contents exposed in air.

The other object of the present invention is to supply one dispenser device comprising a pistol housing, a needle direction control mechanism, a boost mechanism, and a quantification control mechanism wherein the needle direction control mechanism installed at the front end of the pistol housing allows the dispenser device to be easily turned for a precisely controlled direction.

The further object of the present invention is to supply one dispenser device comprising a pistol housing, a needle direction control mechanism, a boost mechanism, and a quantification control mechanism wherein the boost mechanism installed in the pistol housing includes a trigger, a linkage, a front locator, a rear locator, a push rod, a baffle, a magazine release, and a thrust plate. In this regard, the push rod penetrates the front locator, the linkage, the rear locator, and the baffle sequentially; the trigger installed in the pistol housing by a pivot allows its upper end pivoted to the linkage; the baffle on which all acting forces are equilibrated leans against the push rod and contacts to a third spring, the magazine release, and a first stud for a high powerful operation with the trigger pressed driving the push rod shifted and various advantages such as promoted yield rate, assembly easily constructed, reduced manufacture cost, and convenient maintenance.

To reach the above objects, the present invention has principal technical measures described as follows. As one dispenser device, the present invention comprises a pistol housing, a needle direction control mechanism, a boost mechanism, and a quantification control mechanism. In this regard, the pistol housing is provided with a grip for operations by hand; the needle direction control mechanism at the front end of the pistol housing comprises a front cannular retainer, a rear cannular retainer, a cannular sleeve which is accommodated between the front cannular retainer and the rear cannular retainer and containing one spheroid at least, a turning unit steadily coupled with the cannular sleeve, and a propeller housing accommodated in a gap (with a first spring provided at the front end) between the cannular sleeve and the turning unit; the boost mechanism installed in the pistol housing comprises a trigger, a linkage, a front locator, a rear locator, a push rod, a baffle, a magazine release, and a thrust plate wherein the push rod penetrates the front locator, the linkage, the rear locator, and the baffle sequentially and allows its rear end steadily linked to the thrust plate's lower end, the trigger installed in the pistol housing by one pivot allows its upper end linked to the linkage which is opposite to the front locator for one space accommodating a second spring and is against the rear locator with a third spring accommodated between the rear locator and the baffle, so that the baffle on which all acting forces are equilibrated leans against the push rod and contacts to the third spring, the magazine release, and a first stud and the trigger's compressive region and the thrust plate's upper end are displayed on the pistol housing; the quantification control mechanism furnished into the pistol housing comprises an polygonal block, a block locator, and a dosage knob wherein the dosage knob is linked to the polygonal block, which is accommodated between the trigger and the block locator, by a synchro shaft and is displayed on the pistol housing.

The objects of the present invention and the methods to solve technical issues are further fulfilled with the following technical measures.

In the said dispenser device, the pistol housing is constructed with a left housing and a right housing.

In the said dispenser device, the turning unit has its externals with a plurality of grooves and a base which is positioned between the front cannular retainer and the rear cannular retainer, steadily fixed on the pistol housing, and containing a spheroid at least accommodated in a groove corresponding to the turning unit's external.

In the said dispenser device, the needle direction control mechanism comprises a hollow-structured needle tube with a pinhole opened at its front end and a coupling as well as a ring groove at its rear end.

In the said dispenser device, the needle direction control mechanism equipped with a syringe positioning mechanism at the rear end which is fixed on the pistol housing and linked to the rear end of the needle direction control mechanism comprises not less than two syringe inlets in which there is one syringe's sprue linked to the syringe inlet, and the thrust plate is against a plunger of the syringe.

In the said dispenser device, the needle direction control mechanism is equipped with a holding ring at the rear end which is fixed on the pistol housing for an injection direction stabilized, and the thrust plate is against a plunger of the syringe.

In the said dispenser device, the detachable magazine release is installed on the pistol housing and has a taper contacting the baffle.

In the said dispenser device, the block locator is linked to a second stud by a spring holder and against one edge of the polygonal block.

In the said dispenser device, the pivot on the trigger is equipped with a resetting spring with both ends withstanding the trigger and the second stud, respectively.

In the said dispenser device, the quantification control mechanism is capable to precisely control an injected dosage within a range from 1/10 to 1/300 of the maximum capacity of one syringe currently used.

In contrast to prior arts, the present invention of a dispenser device comprising a pistol housing, a needle direction control mechanism, a boost mechanism, a quantification control mechanism, and a syringe positioning mechanism or holding ring is effective in: (1) Uniform injection of agents synchronously and well mixed by not less than two contents which are not exposed in air and high air tightness; (2) Highly precise direction control and easy smooth operation via easy turning; (3) Push rod with shifts driven by a pressed trigger for some advantages such as high powerful operation, promoted yield rate, assembly easily constructed, reduced manufacture cost, and convenient maintenance.

DETAILED DESCRIPTION OF THE PREFERRED EMBODIMENT

Figure 2:
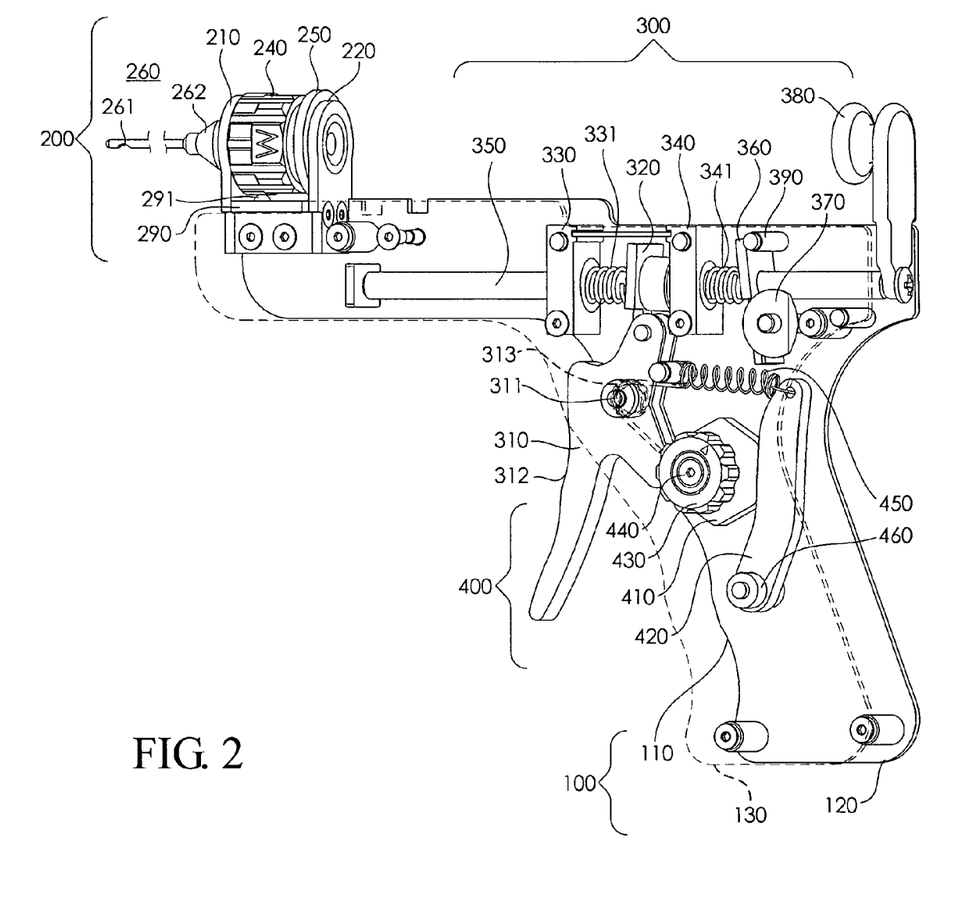
FIG. 2 is a perspective view of the present invention.

For the objects, features, and efficiency of the present invention clearly understood, the preferred embodiments are enumerated hereinafter:

Referring to FIG. 2 which illustrates a dispenser device comprising a pistol housing (100), a needle direction control mechanism (200), a boost mechanism (300), and a quantification control mechanism (400) wherein the pistol housing (100) is provided with a grip (110) for operations by hand, and preferably the pistol housing (100) is constructed with a left housing (120) and a right housing (130).

Figure 3:
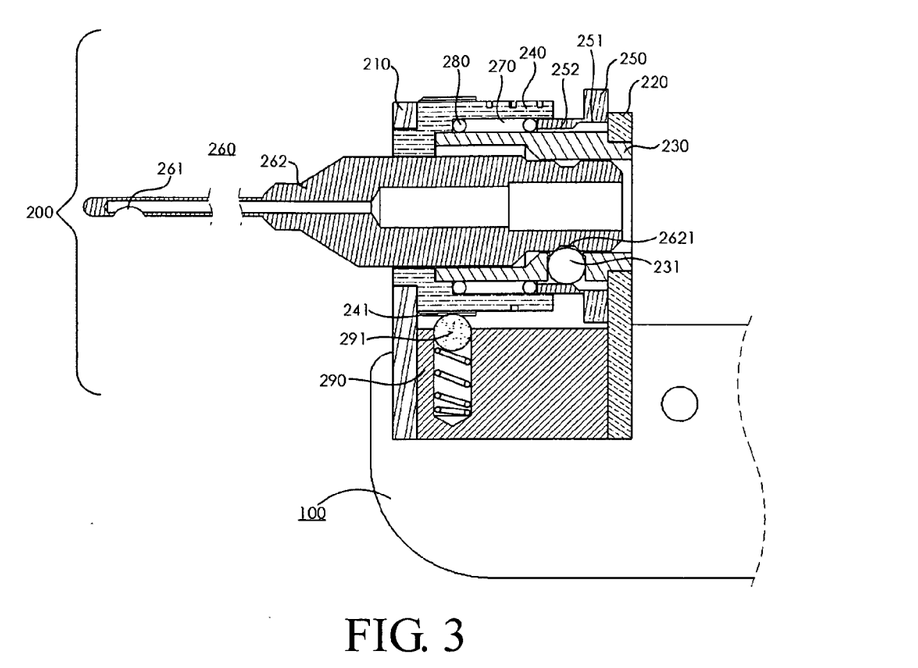
FIG. 3 is a first partial sectional view of the needle direction control mechanism in the present invention.
Figure 4:
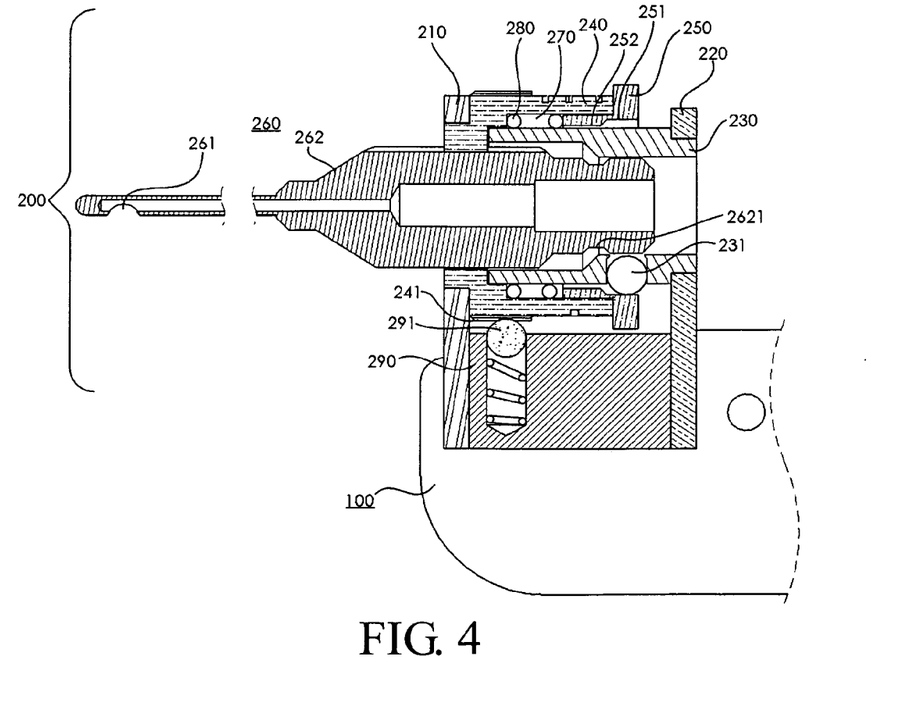
FIG. 4 is a second partial sectional view of the needle direction control mechanism in the present invention.

Referring to FIG. 3 which illustrates a direction control mechanism (200) installed at the front end of the pistol housing (100) comprises a front cannular retainer (210), a rear cannular retainer (220), a cannular sleeve (230), a turning unit (240), a propeller housing (250) and a needle tube (260). In this regard, the cannular sleeve (230) accommodated between the front cannular retainer (210) and the rear cannular retainer (220) is provided with a spheroid (231) at least; the turning unit (240) is steadily linked to a cannular sleeve (230); the propeller housing (250) is accommodated in a gap (270) which is located between the cannular sleeve (230) and the turning unit (240) and provided with a first spring (280) at its front end. In addition, the hollow-structured needle tube (260) has a pinhole (261) at the front end and a coupling (262) with a ring groove (2621) at the rear end. Referring to FIG. 4 which illustrates the propeller housing (250) with the needle tube (260) intentionally linked to the cannular sleeve (230) needs to be pushed toward the front cannular retainer (210) and therefore corresponds to the spheroid (231) of the cannular sleeve (230), and a recess (251) at the inner rim of the propeller housing (250) allows both the spheroid (231) of the cannular sleeve (230) to roll in and the coupling (262) of the needle tube (260) plugged in the cannular sleeve (230). After released, the propeller housing (250) returns to the home position due to bounce of the first spring (280) and allows the spheroid (231) of the cannular sleeve (230) to be against the ring groove (2621) between an inner surface (252) of the propeller housing (250) and the coupling (262) of the needle tube (260) which is steadily accommodated inside the cannular sleeve (230). Preferably, for both the outer surface of the coupling (262) and the inner surface of the cannular sleeve (230) which are not a truly round shape, the turning unit (240) turned by one user synchronously revolves the cannular sleeve (230) and controls directions of the pinhole (261) for a correct angle at injection. Preferably, the outer surface of the turning unit (240) provided with a plurality of grooves (241) and a base (290) between the front cannular retainer (210) and the rear cannular retainer (220) wherein the base (290) is fixed on the pistol housing (100) and contains not less than a spheroid (291) which is against the groove (241) on the outer surface of the corresponding turning unit (240) for an injecting direction of the pinhole (261) stably controlled during rotations of the running unit (240). As a result, an injecting direction of the pinhole (261) is controlled and adjusted according to a user's requirements. Preferably, turning signs such as East (E), West (W), South (S), and North (N) marked on the outer surface of the turning unit (240) is favorable to identifying a position of the pinhole (261) for one user.

Referring to FIG. 2 which illustrates a boost mechanism (300) installed in the pistol housing (100) comprises a trigger (310), a linkage (320), a front locator (330), a rear locator (340), a push rod (350), a baffle (360), a magazine release (370) and a thrust plate (380). In this regard, the push rod (350) penetrating the front locator (330), the linkage (320), the rear locator (340), and the baffle (360) sequentially allows its rear end to be fixed at the lower end of the thrust plate (380); the trigger (310) linked to the pistol housing (100) with a pivot (311) has its upper end connected to the linkage (320) which fits the front locator (330) to accommodate a second spring (331) and is against the rear locator (340) that fits the baffle (360) to accommodate a third spring (341) and makes the baffle (360) on which all acting forces are equilibrated lean against the push rod (350) and contact the third spring (341), the magazine release (370) and a first stud (390); the trigger (310) leaves both upper ends of a compressive region (312) and the thrust plate (380) exposed on the pistol housing (100). A resetting spring (313) installed on the pivot (311) of the trigger (310) has its both ends against the trigger (310) and a second stud (460) and restores the trigger (310) to the home position with the compressive region (312) of the trigger (310) is pressed by one user.

Figure 5:
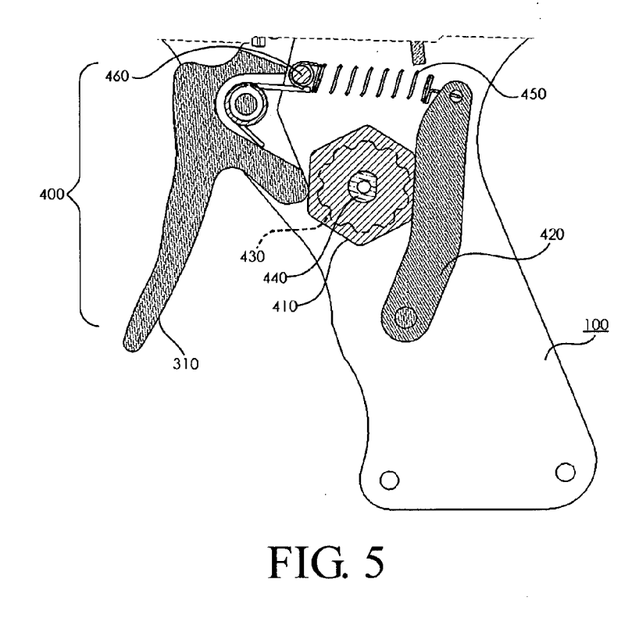
FIG. 5 is a partial sectional view of the quantification control mechanism in the present invention.
Figure 8:
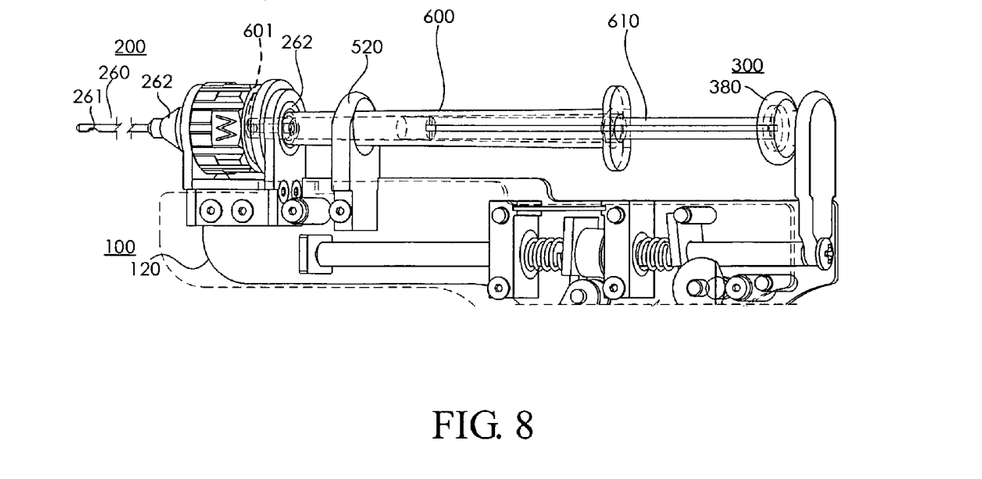
FIG. 8 is a partial perspective view of the third embodiment of the present invention.

Referring to FIG. 5 and FIG. 8 which illustrates that a quantification control mechanism (400) accommodated in the pistol housing (100) comprises a polygonal block (410), a block locator (420), and a dosage knob (430). In this regard, the dosage knob (430) is pivoted to the polygonal block (410) by a synchro shaft (440) and located on the pistol housing (100); the polygonal block (410) is provided between the trigger (310) and the block locator (420); the block locator (420) is connected to the second stud (460) by a spring holder (450) and against one edge of the polygonal block (410). In virtue of different longitudinal distances from any edge of the polygonal block (410) to the pivot center, a mobile interval of the trigger (310) after compression is restricted and is efficient in control of a dosage injected. An injected dosage precisely controlled by the quantification control mechanism (400) between 1/10 and 1/300 of the maximum capacity of the used syringe (600) has its contents in the syringe (600) being fat tissue, hyaluronic acid, collagen, Clostridium botulinum, fluid or semi-fluid medicine, or a combination of these substances hereinabove. Furthermore, a method of combining the synchro shaft (400) and the dosage knob (430) can be fulfilled by a non-orbicular bored spindle and a key, a pin, a hub, or any synchro type element.

Figure 6:
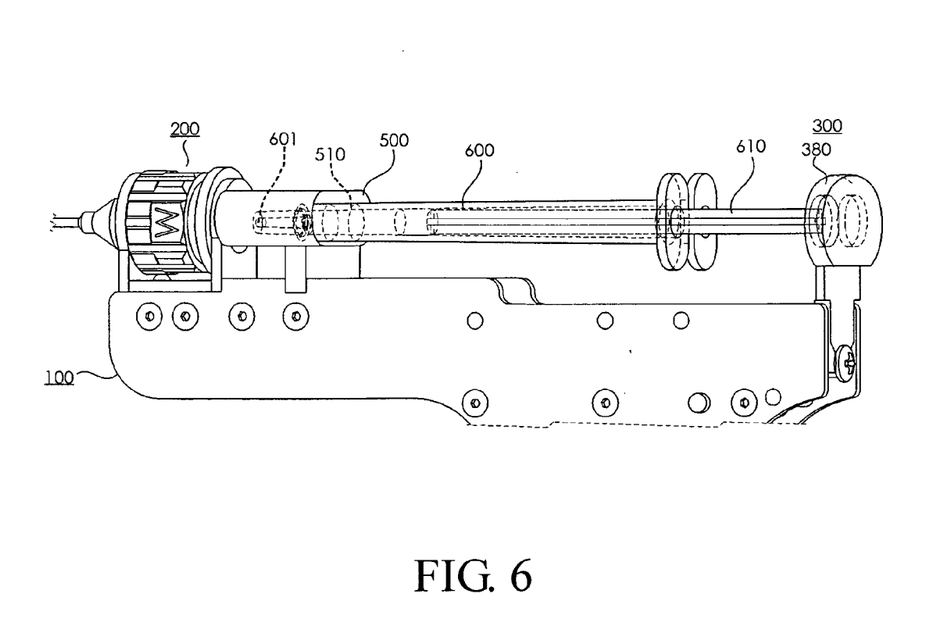
FIG. 6 is a partial perspective view of the second embodiment of the present invention.
Figure 7:
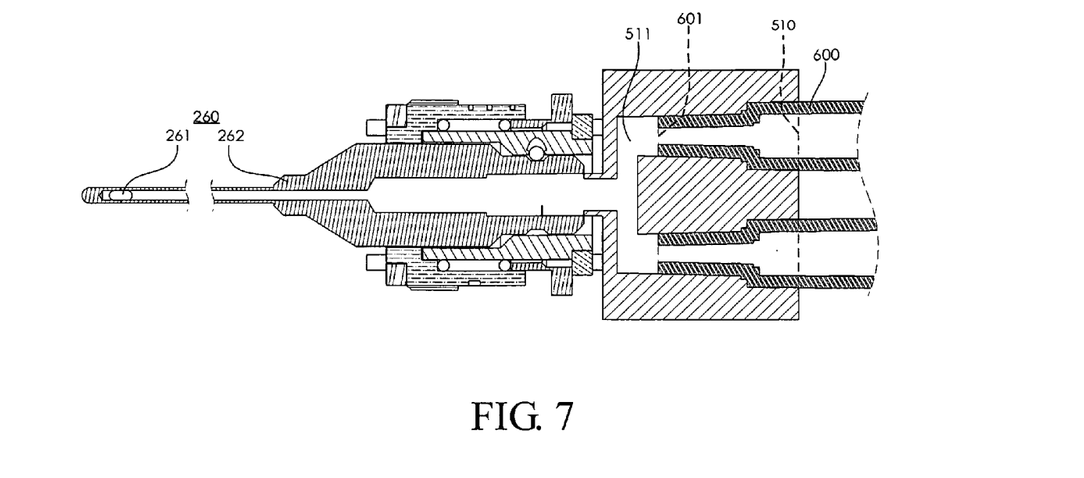
FIG. 7 is a partial sectional view of the second embodiment of the present invention.

Referring to FIG. 6 which illustrates the needle direction control mechanism (200) preferably with its rear end linked to a syringe positioning mechanism (500), which is fixed on the pistol housing (100) and comprises not less than two syringe inlets (510) for the sprue (601) of a syringe (600) at least connected to the syringe inlet (510), and the thrust plate (380) against a plunger (610) which is accommodated in the syringe (600). Referring to FIG. 7 which illustrates the syringe inlet (510) comprises not less than a flow channel (511) linked to the coupling (262) of the needle tube (260) for contents in the syringe (600) injected via the spure (601) of the syringe (600), the flow channel (511), and the pinhole of the needle tube (260).

Referring to FIG. 8 for another embodiment which illustrates a holding ring (520) at the rear end of the needle direction control mechanism (200) is fixed on the pistol housing (100) to stabilize an injecting direction of the syringe (600) and allow both the sprue (601) of the syringe (600) to be linked to the coupling (262) and the thrust plate (380) to be against a plunger (610) of the syringe (600) for contents in the syringe (600) injected via the sprue (601) of the syringe (600) and then the pinhole (261) of the syringe (260).

Figure 9A:
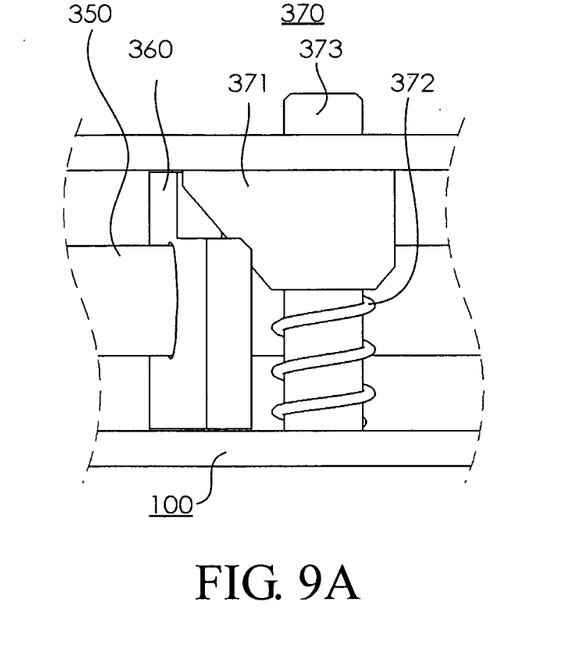
FIG. 9A is a partial view of a magazine release structure in the present invention.
Figure 9B:
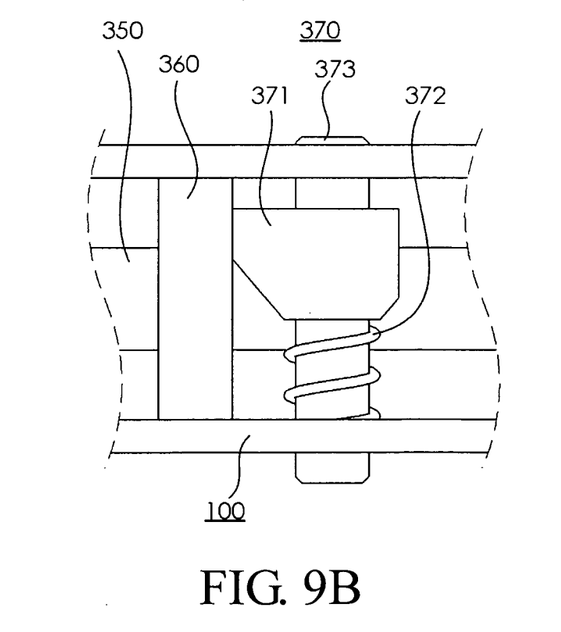
FIG. 9B is a partial view of a magazine release structure pressed in the present invention.

Additionally, referring to FIG. 8, FIG. 9A and FIG. 9B which illustrate the detachable magazine release (370) installed on the pistol housing (100) comprises a taper (371) contacting the baffle (360). Preferably, the magazine release (370) is provided with a fourth spring (372) to make the baffle (360) change a bevel along the outer rim of the taper (371) on the magazine release (370) and be separated from the push rod (350) for the push rod (350) pulled out and another syringe (360) replacing when the outer end (373) of the magazine release (370) is pressed by one user.

With the above descriptions summarized, the present invention comprising a pistol housing, a needle direction control mechanism, a boost mechanism, a quantification control mechanism, and a syringe positioning mechanism or a holding ring fulfills the following characteristics: (1) Uniform injection of agents synchronously and well mixed by not less than two contents which are not exposed in air and high air tightness; (2) Highly precise direction control and easy smooth operation via easy turning; (3) Push rod with shifts driven by a pressed trigger for some advantages such as high powerful operation, promoted yield rate, assembly easily constructed, reduced manufacture cost, and convenient maintenance. Consequently, the present invention different from general dispenser devices but regarded as creative work in contrast to other similar products meets patentability and is applied for the patent.

The foregoing disclosure and description are illustrative and explanatory of preferred embodiments only and therefore any equivalent change in the instruction, claims, or drawings of the present invention does not depart from the scope of the present invention.

What is claimed is:

1. A dispenser device comprising:
    a pistol housing (100) with a grip (110) for operations by hand;
    a needle direction control mechanism (200) installed at a front end of the pistol housing (100) and comprising a front cannular retainer (210), a rear cannular retainer (220), a cannular sleeve (230), a turning unit (240), and a propeller housing (250), wherein the cannular sleeve (230) is accommodated between the front cannular retainer (210) and the rear cannular retainer (220), the cannular sleeve (230) has a spheroid (231), the turning unit (240) is steadily linked to the cannular sleeve (230), the propeller housing (250) is accommodated in a gap (270) between the cannular sleeve (230) and the turning unit (240), the gap (270) is provided with a first spring (280) at the front end;

a boost mechanism (300) installed in the pistol housing (100) comprises a trigger (310), a linkage (320), a front locator (330), a rear locator (340), a push rod (350), a baffle (360), a magazine release (370), and a thrust plate (380) wherein the push rod (350) penetrates the front locator (330), the linkage (320), the rear locator (340), and the baffle (360) and has its rear end linked to a lower end of the thrust plate (380), the trigger (310) is installed in the pistol housing (100) by a pivot (311) and allows its upper end pivoted to the linkage (320) which fits the front locator (330) to accommodate a second spring (331) and is against the rear locator (340) that fits the baffle (360) to accommodate a third spring (341) and makes the baffle (360) on which all acting forces are equilibrated lean against the push rod (350) and contact the third spring (341), the magazine release (370) and a first stud (390), a compressive region (312) on the trigger (310) along with the thrust plate (380) are displayed on the pistol housing (100); and a quantification control mechanism (400) installed in the pistol housing (100) comprises a polygonal block (410), a block locator (420), and a dosage knob (430) wherein the dosage knob (430) is linked to the polygonal block (410) by a synchro shaft (440) and installed on the pistol housing (100) and the polygonal block (410) is accommodated between the trigger (310) and the block locator (420);

wherein the turning unit (240) is provided with a plurality of grooves (241) on an outer surface and a base (290) which is positioned between the front cannular retainer (210) and the rear cannular retainer (220), fixed on the pistol housing (100), and has not less than a spheroid (291) accommodated in the grooves (241) on the outer surface of the corresponding turning unit (240).

2. The dispenser device according to claim 1, wherein the pistol housing (100) is constructed with a left housing (120) and a right housing (130).

3. The dispenser device according to claim 1, wherein the needle direction control mechanism (200) comprises a hollow needle tube (260) with a pinhole (261) at a front end of the hollow needle tube and a coupling (262) with a ring groove (2621) at a rear end of the hollow needle tube.

4. The dispenser device according to claim 1, wherein a rear end of the needle direction control mechanism (200) is linked to a syringe positioning mechanism (500) which is fixed on the pistol housing (100) and comprises not less than two syringe inlets (510) to allow a sprue (601) of a syringe (600) at least to be connected to one of the not less than two syringe inlets (510), and the thrust plate (380) is against a plunger (610) of the syringe (600).

5. The dispenser device according to claim 1, wherein a rear end of the needle direction control mechanism (200) is provided with a holding ring (520) which is fixed on the pistol housing (100) to stabilize an injecting direction of a syringe (600), and the thrust plate (380) is against a plunger (610) of the syringe (600).

6. The dispenser device according to claim 1, wherein the magazine release (370) installed on the pistol housing (100) has a taper (371) contacting the baffle (360).

7. The dispenser device according to claim 6, wherein the pivot (311) of the trigger (310) is provided with a resetting spring (313) with both ends against the trigger (310) and a second stud (460).

8. The dispenser device according to claim 1, wherein the block locator (420) is linked to a second stud (460) by a spring holder (450) and is against one edge of the polygonal block (410).

9. The dispenser device according to claim 1, wherein a dosage injected by the quantification control mechanism (400) is precisely controlled in a range from $1/10$ to $1/300$ of a maximum capacity of a used syringe (600).

* * * * *